US012514580B2

(12) United States Patent

Zhou et al.

(10) Patent No.: US 12,514,580 B2

(45) Date of Patent: Jan. 6, 2026

(54) POWERED STAPLING DEVICE WITH MANUAL OVERRIDE MECHANISM

(71) Applicant: Covidien LP, Mansfield, MA (US)

(72) Inventors: Xiao Zhou, Shanghai (CN); Shouwei Li, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/866,710

(22) PCT Filed: May 24, 2022

(86) PCT No.: PCT/CN2022/094775

§ 371 (c)(1),
(2) Date: Nov. 18, 2024

(87) PCT Pub. No.: WO2023/225866

PCT Pub. Date: Nov. 30, 2023

(65) Prior Publication Data

US 2025/0325265 A1 Oct. 23, 2025

(51) Int. Cl.
*A61B 17/072* (2006.01)
*A61B 17/00* (2006.01)

(52) U.S. Cl.
CPC .................. *A61B 17/07207* (2013.01); *A61B 2017/00398* (2013.01)

(58) Field of Classification Search
CPC ................................................ A61B 17/07207
See application file for complete search history.

(56) References Cited

U.S. PATENT DOCUMENTS

| | | | |
|---|---|---|---|
| 2016/0287256 A1 | 10/2016 | Marczyk | |
| 2017/0135748 A1 | 5/2017 | Aldridge et al. | |
| 2017/0290583 A1 | 10/2017 | Reed et al. | |
| 2022/0000479 A1 | 1/2022 | Shelton, IV et al. | |
| 2022/0031321 A1* | 2/2022 | Sun | A61B 17/07207 |

FOREIGN PATENT DOCUMENTS

| | | |
|---|---|---|
| CN | 102083373 A | 6/2011 |
| CN | 202776434 U | 3/2013 |
| CN | 103747748 A | 4/2014 |
| CN | 107809966 A | 3/2018 |
| CN | 113907822 A | 1/2022 |
| WO | 2020077531 A1 | 4/2020 |

OTHER PUBLICATIONS

PCT International Search Report and Written Opinion, mailed Feb. 15, 2023, 12 pages.
Extended European Search Report for European Patent Application No. 22943072.3 mailed Nov. 4, 2025, 9 pages.

* cited by examiner

*Primary Examiner* — Nathaniel C Chukwurah

(57) ABSTRACT

A surgical device (10) includes a powered handle assembly (12) that is coupled to a tool assembly (16) by an elongate body (14). The powered handle assembly (12) includes a motor assembly (46) that is coupled to a toothed rack (48) by a gear assembly (51). The motor assembly (46) can be actuated to advance or retract the toothed rack (48) to actuate the tool assembly (16). The handle assembly (12) includes a housing (18) that defines an opening (84) that is dimensioned to receive a retraction tool (90) that is configured to engage the gear assembly (51) and manually override the motor assembly (46) to facilitate manual retraction of the toothed rack (48).

20 Claims, 6 Drawing Sheets

POWERED STAPLING DEVICE WITH MANUAL OVERRIDE MECHANISM

CROSS-REFERENCE TO RELATED APPLICATIONS

This application is a National Stage Application of PCT/CN2022/094775 filed 24 May 2022, the entire content of which is incorporated herein by reference.

FIELD

This disclosure is directed to powered surgical devices and, more particularly, to powered surgical devices with manual override mechanisms.

BACKGROUND

Various types of surgical devices used to endoscopically treat tissue are known in the art, and are commonly used, for example, for closure of tissue or organs in transection, resection, and anastomoses procedures, for occlusion of organs in thoracic and abdominal procedures, and for electrosurgically fusing or sealing tissue.

One example of such a surgical device is a surgical stapling device. Typically, surgical stapling devices include a tool assembly having an anvil assembly and a cartridge assembly, and a drive assembly. The drive assembly includes a flexible drive beam and a clamp member that is supported on a distal end of the drive beam. The drive assembly is movable to advance the clamp member through the tool assembly to approximate the cartridge and anvil assemblies and to advance an actuation sled through the cartridge assembly to eject staples from the cartridge assembly.

Surgical stapling devices can be manually actuated devices in which a clinician squeezes a trigger to actuate the stapling device, or powered stapling devices in which a clinician activates a motor within the stapling device to actuate the stapling device. Although powered stapling devices require less force to operate, difficulties may arise when the device loses power or components of the device malfunction or become damaged. In such instances, the device remains clamped about tissue preventing removal of the device from a patient.

A continuing need exists in the art for a powered stapling device that includes a drive assembly that can be manually retracted when power is lost or when the device is not operational to facilitate removal from a patient.

SUMMARY

A surgical device includes a powered handle assembly that is coupled to a tool assembly by an elongate body. The powered handle assembly includes a motor assembly that is coupled to a toothed rack by a gear assembly. The motor assembly can be actuated to advance or retract the toothed rack to actuate the tool assembly. The handle assembly includes a housing that defines an opening that receives a retraction tool that is configured to engage the gear assembly and manually override the motor assembly to facilitate manual retraction of the toothed rack.

Aspects of the disclosure are directed to a powered handle assembly for a surgical device that includes a housing, a motor assembly, a toothed rack, a gear shaft, a spur gear, and a bevel gear. The housing defines a cavity and an opening that communicates with the cavity. The motor assembly is supported within the cavity of the housing and includes a motor shaft and an output gear secured to the motor shaft. The toothed rack is received within the cavity of the housing and is supported for longitudinal movement between retracted and advanced positions. The gear shaft is supported within the cavity of the housing. The spur gear is rotatably supported on the gear shaft and linearly movable along the gear shaft between first and second positions. The spur gear includes a gear member and a cylindrical shaft portion. The gear member is engaged with the toothed rack such that rotation of the spur gear causes longitudinal movement of the toothed rack between the retracted and advanced positions. The bevel gear is rotatably supported about the gear shaft and is engaged with the output gear of the motor assembly. The spur gear is engaged with the bevel gear when the spur gear is in the first position and disengaged from the bevel gear when the spur gear is in the second position such that rotation of the bevel gear causes rotation of the spur gear when the spur gear is in the first position to move the toothed rack longitudinally between the retracted and advanced positions.

In aspects of the disclosure, the handle assembly includes a biasing member that is positioned to urge the spur gear towards the first position.

In some aspects of the disclosure, the powered handle assembly includes a retraction tool that is dimensioned to be received through the opening in the housing to move the spur gear from the first position to the second position.

In certain aspects of the disclosure, the cylindrical shaft portion of the spur gear includes a first end spaced from the gear member that is configured to couple to the retraction tool such that rotation of the retraction tool with the spur gear in the second position causes rotation of the spur gear independently of the bevel gear.

In aspects of the disclosure, the retraction tool includes a shaft and a handle coupled to the shaft, and the shaft of the retraction tool has a first end spaced from the handle that is configured to couple to the first end of the cylindrical shaft portion of the spur gear.

In some aspects of the disclosure, the first end of the shaft of the retraction tool and the first end of the cylindrical shaft portion of the spur gear include castellations that engage each other such that rotation of the retraction tool causes corresponding rotation of the spur gear.

In certain aspects of the disclosure, the bevel gear is supported about the cylindrical shaft portion of the spur gear.

In aspects of the disclosure, a bearing is supported on the bevel gear and positioned about the cylindrical shaft portion of the spur gear.

In some aspects of the disclosure, the spur gear supports protrusions, the bevel gear defines cutouts, and the protrusions are received within the cutouts when the spur gear is in the first position to couple the spur gear to the bevel gear.

Other aspects of the disclosure are directed to a surgical device that includes a powered handle assembly, an elongate body, and a tool assembly. The powered handle assembly includes a housing, a motor assembly, a toothed rack, a gear shaft, a spur gear, and a bevel gear. The housing defines a cavity and an opening that communicates with the cavity. The motor assembly is supported within the cavity of the housing and includes a motor shaft and an output gear that is secured to the motor shaft. The toothed rack is received within the cavity of the housing and is supported for longitudinal movement between retracted and advanced positions. The gear shaft is supported within the cavity of the housing. The spur gear is rotatably supported on the gear shaft and linearly movable along the gear shaft between first and second positions. The spur gear includes a gear member and a cylindrical shaft portion. The gear member is engaged with the toothed rack such that rotation of the spur gear causes longitudinal movement of the toothed rack between the retracted and advanced positions. The bevel gear is rotatably supported about the gear shaft and is engaged with the output gear of the motor assembly. The spur gear is engaged with the bevel gear when the spur gear is in the first position and disengaged from the bevel gear when the spur gear is in the second position such that rotation of the bevel gear causes rotation of the spur gear when the spur gear is in the first position to move the toothed rack longitudinally between the retracted and advanced positions. The elongate body includes a firing rod that is coupled to the toothed rack and has a proximal portion and a distal portion. The proximal portion of the elongate body is coupled to the powered handle assembly. The tool assembly is supported on the distal portion of the elongate body.

In aspects of the disclosure, the tool assembly includes an anvil and a cartridge assembly. Other features of the disclosure will be appreciated from the following description.

BRIEF DESCRIPTION OF THE DRAWINGS

Various aspects of the disclosed surgical device are described herein below with reference to the drawings, wherein.

DETAILED DESCRIPTION

Figure 1:
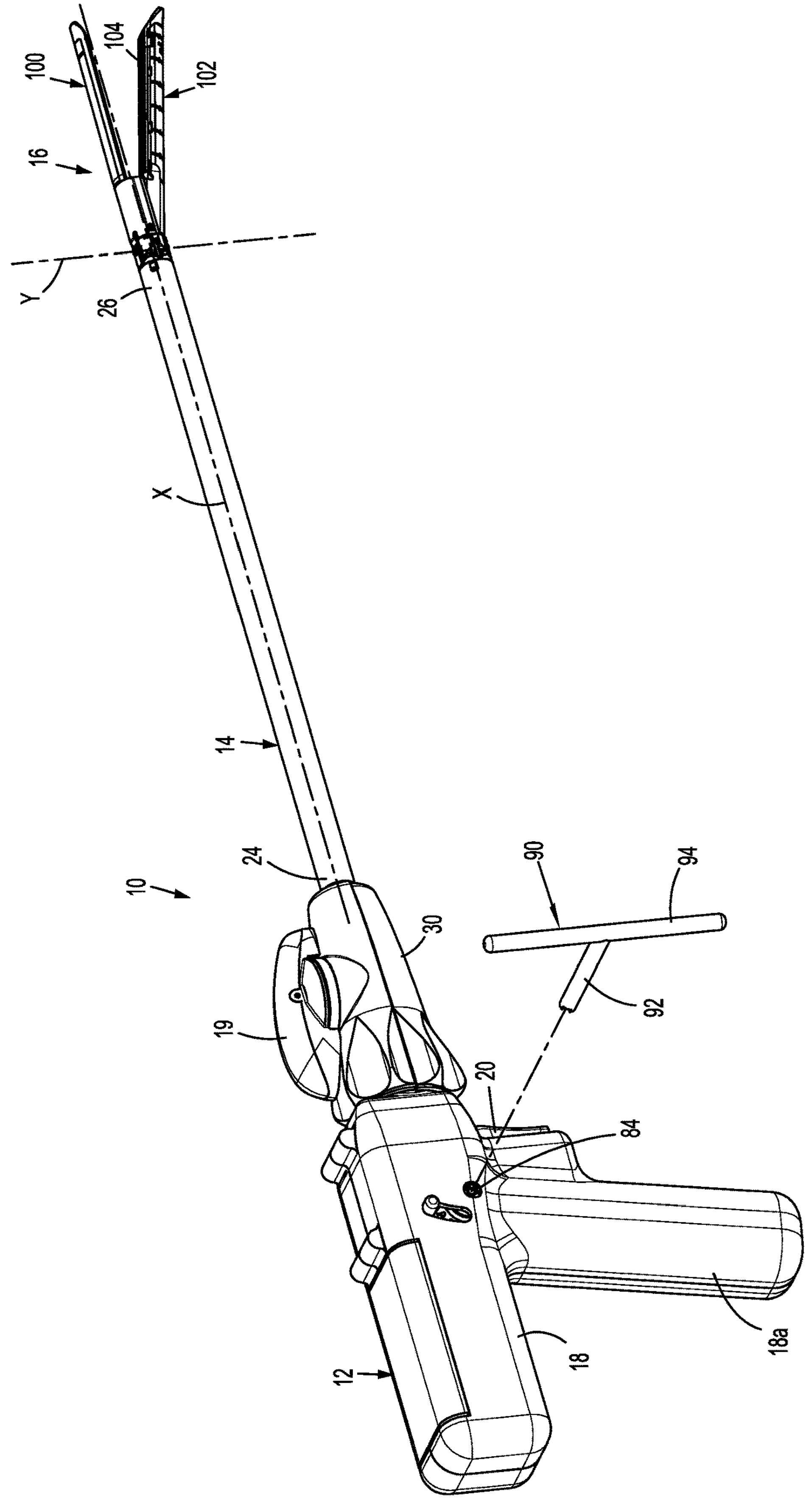
FIG. 1 is a side perspective view of a surgical device according to aspects of the disclosure with a tool assembly of the surgical device in a non-articulated, unclamped position.

The disclosed surgical device will now be described in detail with reference to the drawings in which like reference numerals designate identical or corresponding elements in each of the several views. However, it is to be understood that aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, and similar terms are used to assist in understanding the description and are not intended to limit the disclosure.

In this description, the term "proximal" is used generally to refer to that portion of the device that is closer to a clinician during use of the device in its customary fashion, while the term "distal" is used generally to refer to that portion of the device that is farther from the clinician during use of the device in its customary fashion. In addition, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, surgeons, and support personnel.

This disclosure is directed to a surgical device that includes a powered handle assembly that is coupled to a tool assembly by an elongate body. The powered handle assembly includes a motor assembly that is coupled to a toothed rack by a gear assembly. The motor assembly can be actuated to advance or retract the toothed rack to actuate the tool assembly. The handle assembly includes a housing that defines an opening that receives a retraction tool that is configured to engage the gear assembly and manually override the motor assembly to facilitate manual retraction of the toothed rack.

FIG. 1 illustrates a surgical device shown generally as stapling device 10. The stapling device 10 includes a handle assembly 12, an elongate body 14, and a tool assembly 16. The handle assembly 12 includes a housing 18 that forms a stationary handle portion **18*a*, an articulation lever 19, and an actuation button 20. The housing 18 of the handle assembly 12 is formed from half-sections that are coupled together such as by welding or with screws to define a cavity 38 (FIG. 2) that receives internal components of the handle assembly 12** which are described in further detail below.

The elongate body 14 defines a longitudinal axis "X" and includes a proximal portion 24 that is coupled to the handle assembly 12, and a distal portion 26 that supports the tool assembly 16. The tool assembly 16 is secured to the distal portion 26 of the elongate body 14 by a pivot member 28 that defines an axis "Y" that is transverse to the longitudinal axis "X". The articulation lever 19 is operatively coupled to the tool assembly 16 via an articulation linkage (not shown) such that manipulation of the articulation lever 19 causes articulation of the tool assembly 16 about the axis "Y" between a non-articulated position in which the tool assembly 16 defines a longitudinal axis that is aligned with the longitudinal axis "X" and non-articulated positions in which a longitudinal axis of the tool assembly 16 and the longitudinal axis "X" of the elongate body 14 define acute angles.

The proximal portion 24 of the elongate body 14 is supported within a rotation knob 30 that is rotatably coupled to a distal portion of the handle assembly 12. The rotation knob 30 is manually rotatable about the longitudinal axis "X" to rotate the elongate body 14 and the tool assembly 16 about the longitudinal axis "X". The actuation button 20 controls operation of the different functions of the stapling device 10 including clamping and firing of the stapling device 10.

Figure 2:
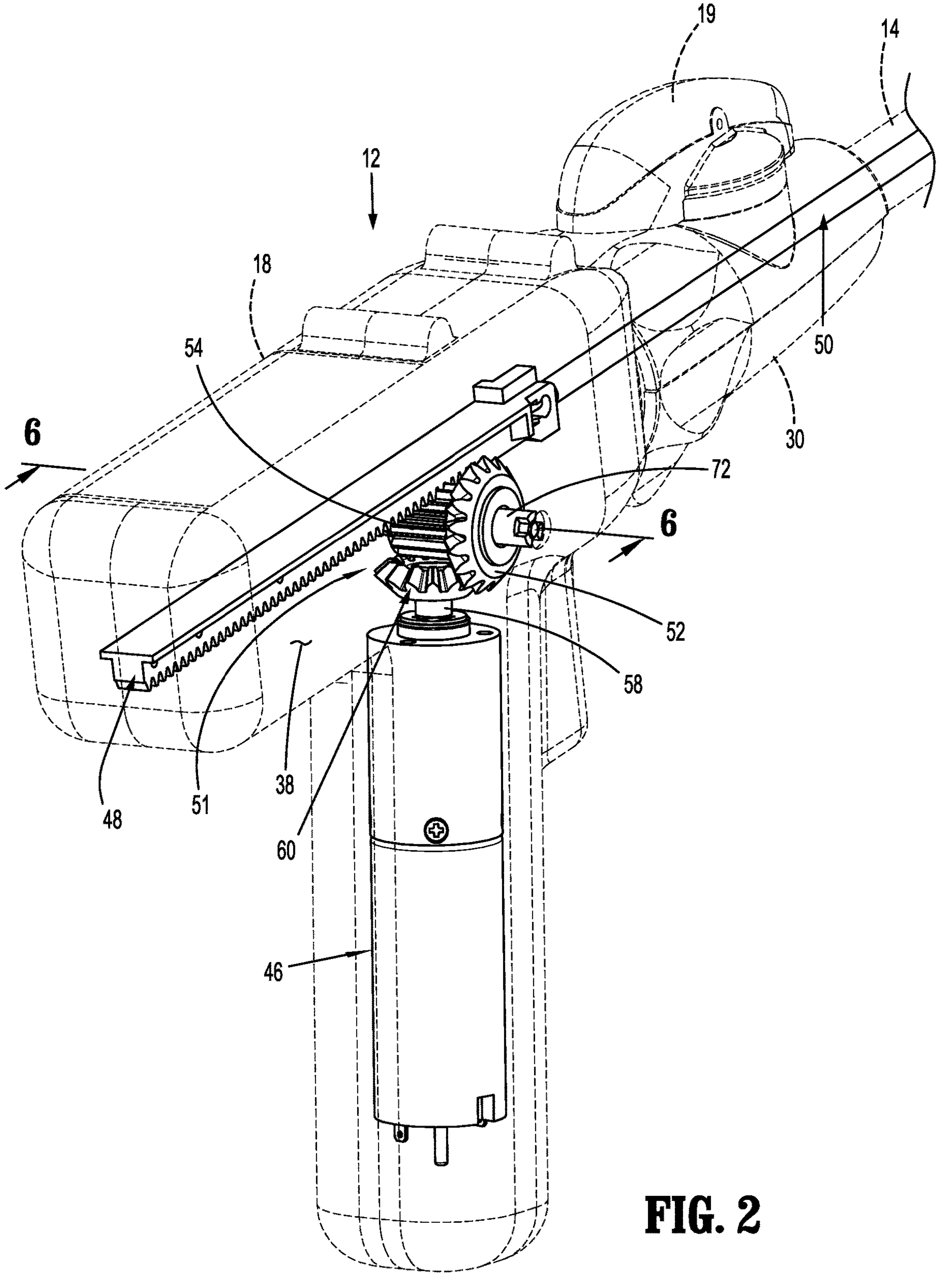
FIG. 2 is a perspective view from a proximal end of a handle assembly of the surgical device shown in FIG. 1 with a housing of the handle assembly shown in phantom illustrating internal components of the handle assembly including a motor assembly, a toothed rack, a spur gear, and a bevel gear.
Figure 3:
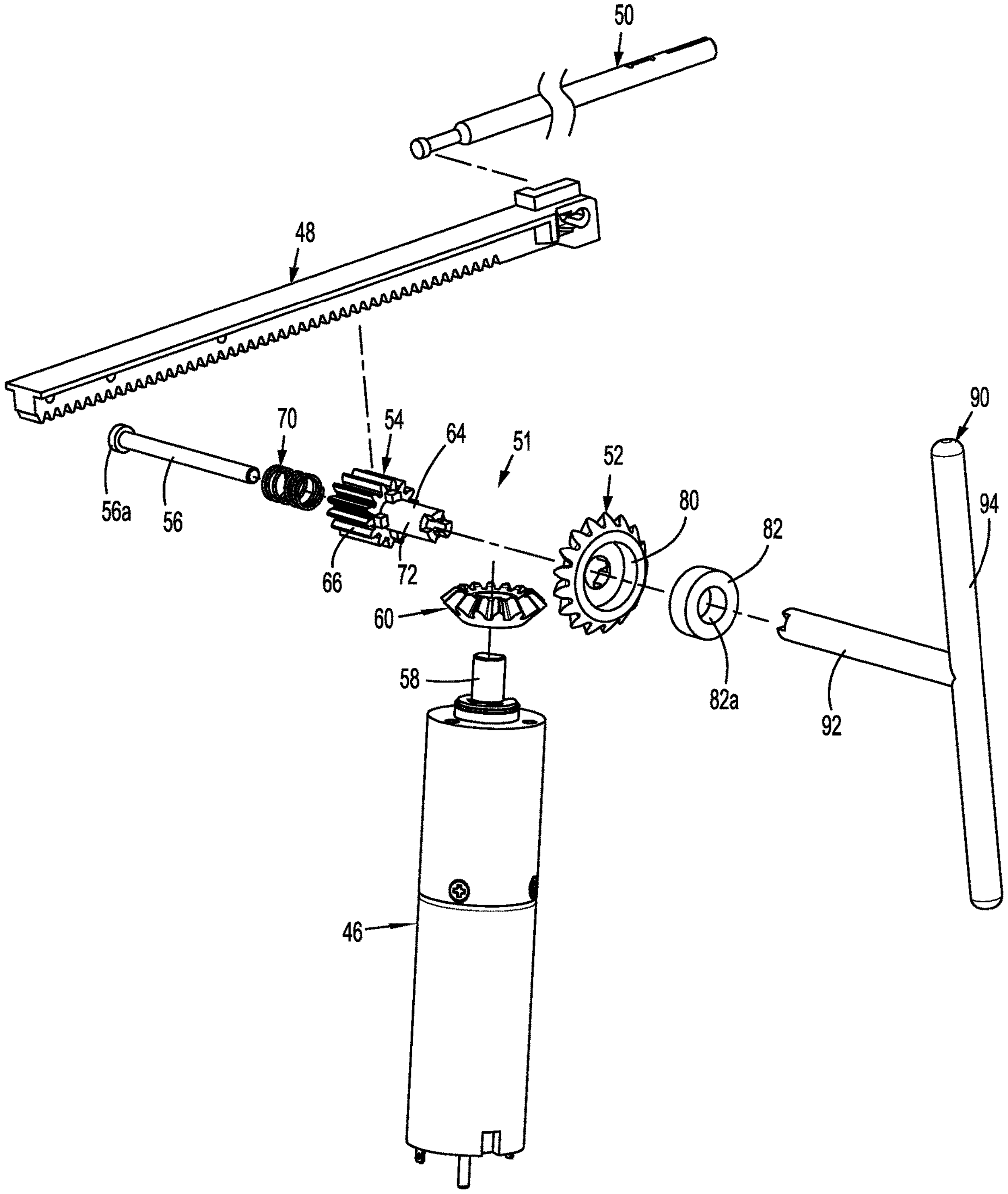
FIG. 3 is an exploded, perspective view of the internal components of the handle assembly shown in FIG. 2 in association with a retraction tool.

FIGS. 2 and 3 illustrate internal components of the handle assembly 12 (FIG. 1) which include a motor assembly 46, a toothed rack 48, a firing rod 50, and a gear assembly 51. The toothed rack 48 is coupled to the firing rod 50 such that longitudinal movement of the toothed rack 48 causes longitudinal movement of the firing rod 50. The gear assembly 51 includes a bevel gear 52, a spur gear 54, and a gear shaft 56. The motor assembly 46 includes a motor shaft 58 that supports an output gear 60 that is engaged with the bevel gear 52 of the gear assembly 51. The output gear 60 is fixedly secured to the motor shaft 58 such that rotation of the motor shaft 58 causes corresponding rotation of the output gear 60. When the motor assembly 46 is activated by pressing the actuation button 20 (FIG. 1), rotation of the motor shaft 58 rotates the drive gear 56 to rotate the bevel gear 52. In aspects of the disclosure, the motor assembly 46 is positioned within a portion of the cavity 38 (FIG. 2) of the housing 18 defined by the stationary handle portion 18*a* (FIG. 3).

The bevel gear 52 and the spur gear 54 are rotatably supported within the housing 18 of the handle assembly 12 (FIG. 1) on the gear shaft 56. The gear shaft 56 is supported within the cavity 38 (FIG. 2) of the housing 18 of the handle assembly 12 and defines an axis that is substantially perpendicular to the longitudinal axis "X" defined by the elongate body 14. One end of the gear shaft 56 includes a head portion 56*a* that has a diameter that is larger than the remining portion of the gear shaft 56. In aspects of the disclosure, the gear shaft 56 is rotatably supported on the housing 18 of the handle assembly 12 or on a gear casing (not shown) supported within the housing 18. In aspects of the disclosure, the head portion 56*a* is supported within a recess 71 (FIG. 6) defined in the housing 18 of the handle assembly 12 to support the gear shaft 56 within the cavity 38 (FIG. 2) of the handle assembly 12.

Figure 4:
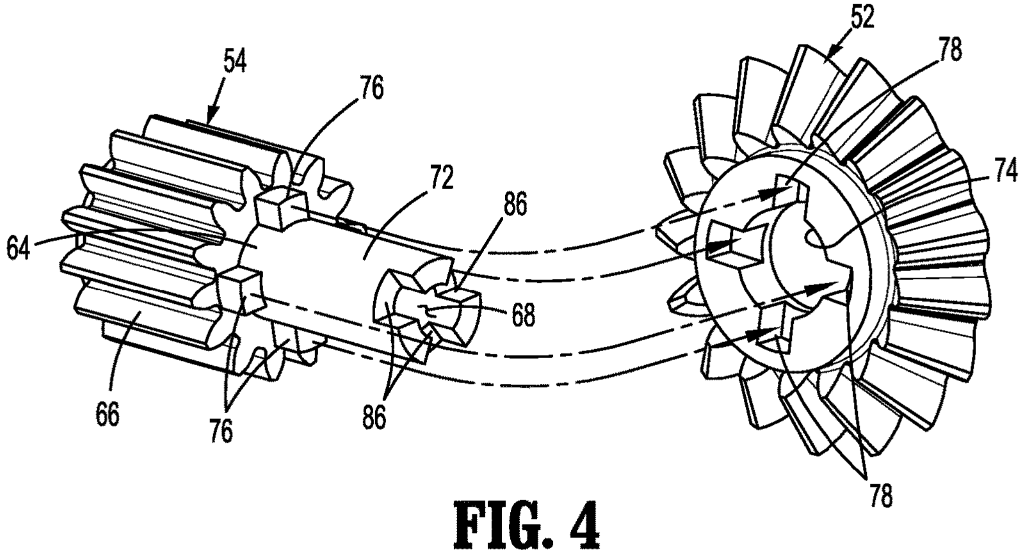
FIG. 4 is a side perspective view of the spur gear and the bevel gear of the handle assembly shown in FIG. 2 with parts separated.
Figure 5:
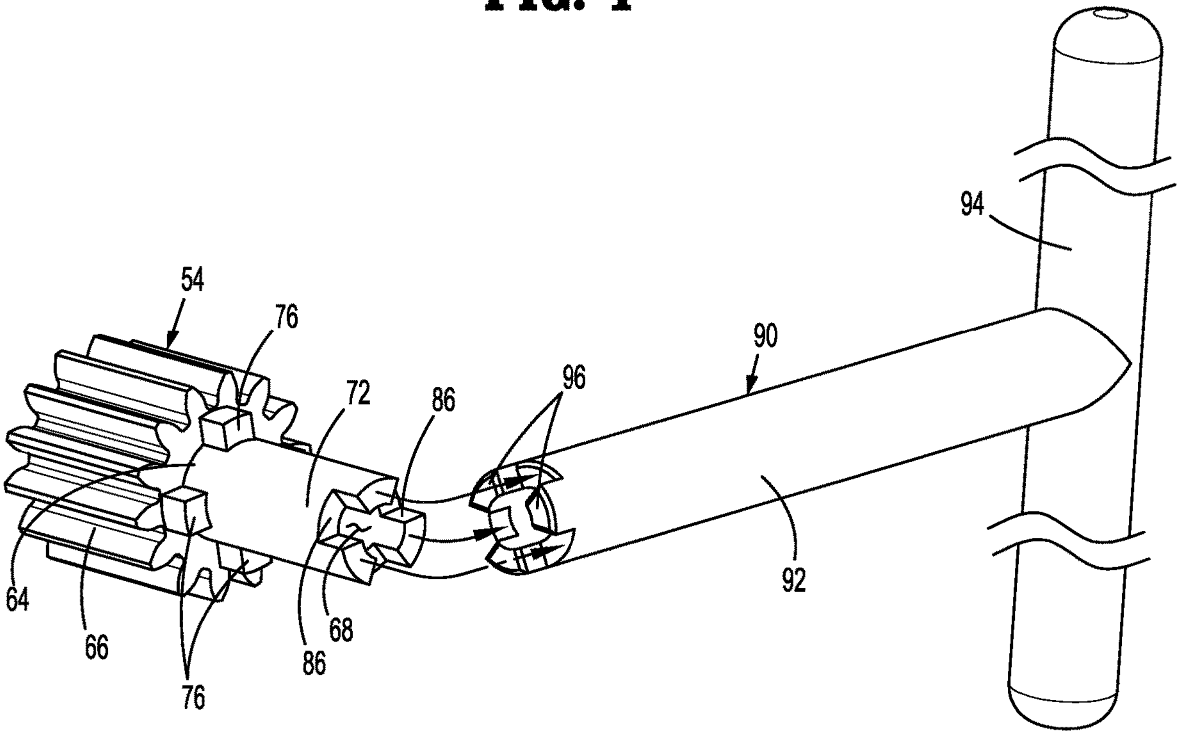
FIG. 5 is a side perspective view of the spur gear of the handle assembly and the retraction tool shown in FIG. 3 with parts separated.

FIGS. 4 and 5 illustrate the spur gear 54 which includes a central hub portion 64 and a gear member 66 that is formed about the central hub portion 64. The central hub portion 64 of the spur gear 54 defines a through bore 68 (FIG. 5) that receives the gear shaft 56 such that the spur gear 54 is rotatably supported on the gear shaft 56. The spur gear 54 is movable along the gear shaft 56 between first and second positions. In the first position (FIG. 6), the spur gear 54 is engaged with the bevel gear 52 and in the second position (FIG. 9), the spur gear 54 is disengaged from the bevel gear 52. In aspects of the disclosure, a biasing member 70 is positioned between the head portion 56*a* of the gear shaft 56 and the spur gear 54 to urge the spur gear 54 towards the first position engaged with the bevel gear 52.

The central hub portion 64 of the spur gear 54 extends outwardly of the gear member 66 and defines a cylindrical shaft portion 72. The cylindrical shaft portion 72 of the spur gear 54 extends through a central opening 74 (FIG. 4) of the bevel gear 52 and includes protrusions 76 that are positioned adjacent the gear member 66. The protrusions 76 of the spur gear 54 are received within cutouts 78 (FIG. 4) formed about the central opening 74 in the bevel gear 52 when the spur gear 54 is in the first position to secure the spur gear 54 to the bevel gear 52. In aspects of the disclosure, the spur gear includes four protrusions, and the bevel gear includes four cutouts. When the protrusions 76 of the spur gear 54 are received within the cutouts 78 of the bevel gear 52, rotation of the bevel gear 52 causes corresponding rotation of the spur gear 54. In aspects of the disclosure, the bevel gear 52 defines a cylindrical recess 80 that receives a bearing 82 (FIG. 3). The bearing 82 defines a central through bore 82*a* that receives the cylindrical shaft portion 72 of the spur gear 54 and rotatably supports the bevel gear 52 on the spur gear 54.

The cylindrical shaft portion 72 of the spur gear 54 extends from the gear member 66 of the spur gear 54 outwardly into or adjacent an opening 84 (FIG. 1) defined in the housing 18 of the handle assembly 12. The opening in the housing 18 of the handle assembly 12 is aligned with the cylindrical shaft portion 72 of the spur gear 54. An end of the cylindrical shaft portion 72 opposite to the gear member 66 defines first castellations 86 that are positioned within the opening 84 of the housing 18 of the handle assembly 12. The first castellations 86 on the cylindrical shaft portion 72 of the spur gear 54 are configured to engage a retraction tool 90 as described below such that rotation of the retraction tool 90 causes rotation of the spur gear 54.

FIG. 5 illustrates the retraction tool 90 which includes a shaft 92 and a handle 94. The shaft 92 is substantially linear and is received through the opening 84 (FIG. 1) in the housing 18 of the handle assembly 12 into engagement with the spur gear 54. More specifically, the shaft 92 of the retraction tool 90 includes an end opposite to the handle 94 of the retraction tool 90 that defines second castellations 96. The castellations 96 of the retraction tool 90 are configured to engage or mesh with the castellations 86 of the spur gear 54 to rotatably fix the retraction tool 90 to the spur gear 54 such that rotation of the retraction tool 90 causes corresponding rotation of the spur gear 54. It is envisioned that the spur gear 54 and the retraction tool 90 may have a variety of different interlocking or engaging configurations that rotatably fix the retraction tool 90 to the spur gear 54 such that rotation of the retraction tool 90 causes corresponding rotation of the spur gear 54.

In aspects of the disclosure, the tool assembly 16 is in the form of a stapling device and includes an anvil 100 and a cartridge assembly 102. The cartridge assembly 100 has a staple cartridge 104 that supports a plurality of staples (not shown) and is movable in relation to the anvil 100 between an open position (FIG. 1) and a clamped position (FIG. 7) to clamp tissue "T" between the anvil 100 and the cartridge assembly 102. It is envisioned that the tool assembly 16 could have a variety of different forms to perform a variety of different surgical operations. For example, the tool assembly 16 could include a vessel sealing device or a clip applying device.

Figure 7:
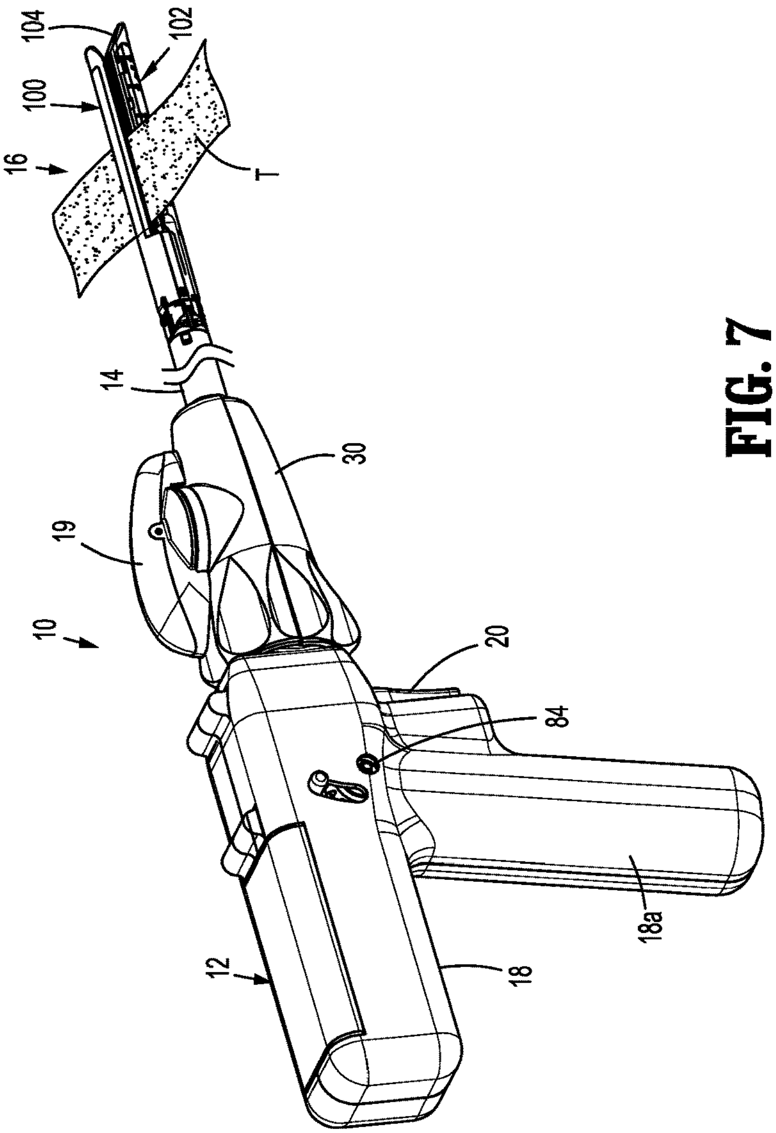
FIG. 7 is a side perspective view of the surgical device shown in FIG. 1 with the surgical device in a clamped position.
Figure 6:
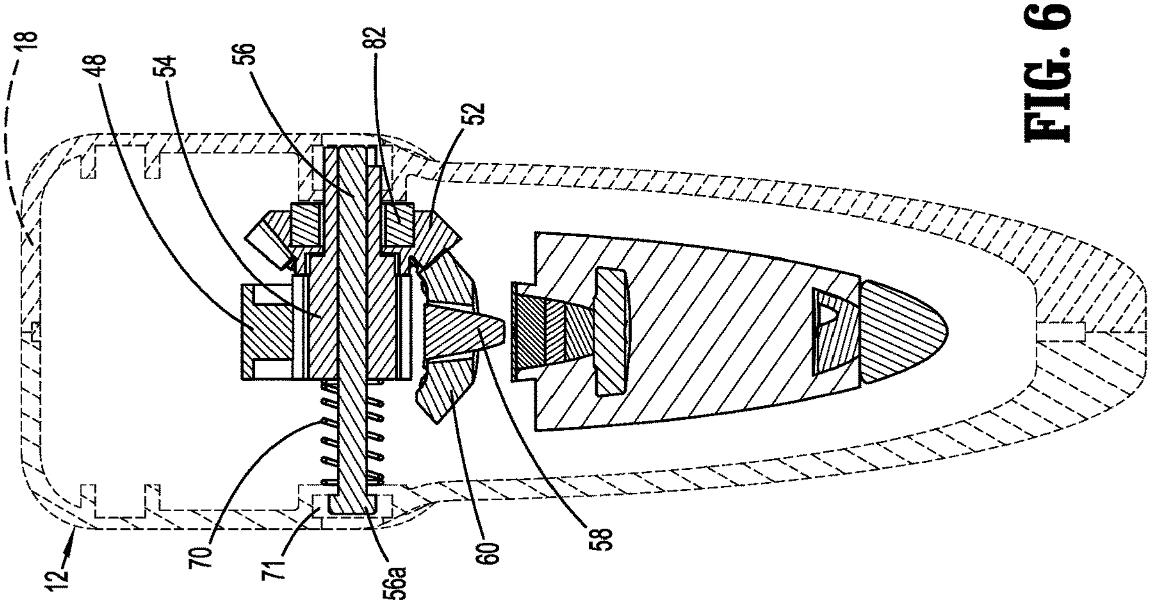
FIG. 6 is a cross-sectional view taken along section line 6-6 of FIG. 2.

FIGS. 6 and 7 illustrate the handle assembly 12 with the spur gear 54 in the first position. When the powered handle assembly 12 is operating in its intended fashion, the spur gear 54 is urged by the biasing member 70 into engagement with the bevel gear 52. When the spur gear 54 is engaged with the bevel gear 52, the protrusions 76 (FIG. 4) of the spur gear 54 are received in the cutouts 78 of the bevel gear 52 such that rotation of the bevel gear 52 causes corresponding rotation of the spur gear 54. As described above, the bevel gear 52 is engaged with the output gear 60 of the motor assembly 46 (FIG. 3) and the spur gear 54 is engaged with the toothed rack 48. Thus, when the motor assembly 46 is activated, the output gear 60 of the motor assembly 46 rotates the bevel gear 52 to rotate the spur gear 54. When the spur gear 54 rotates, the toothed rack 48 is moved linearly within the cavity 38 of the housing 18 of the handle assembly 12 to advance the firing rod 50. The firing rod 50 is coupled to the tool assembly 16 to actuate the tool assembly upon advancement of the firing rod 50.

Figure 9:
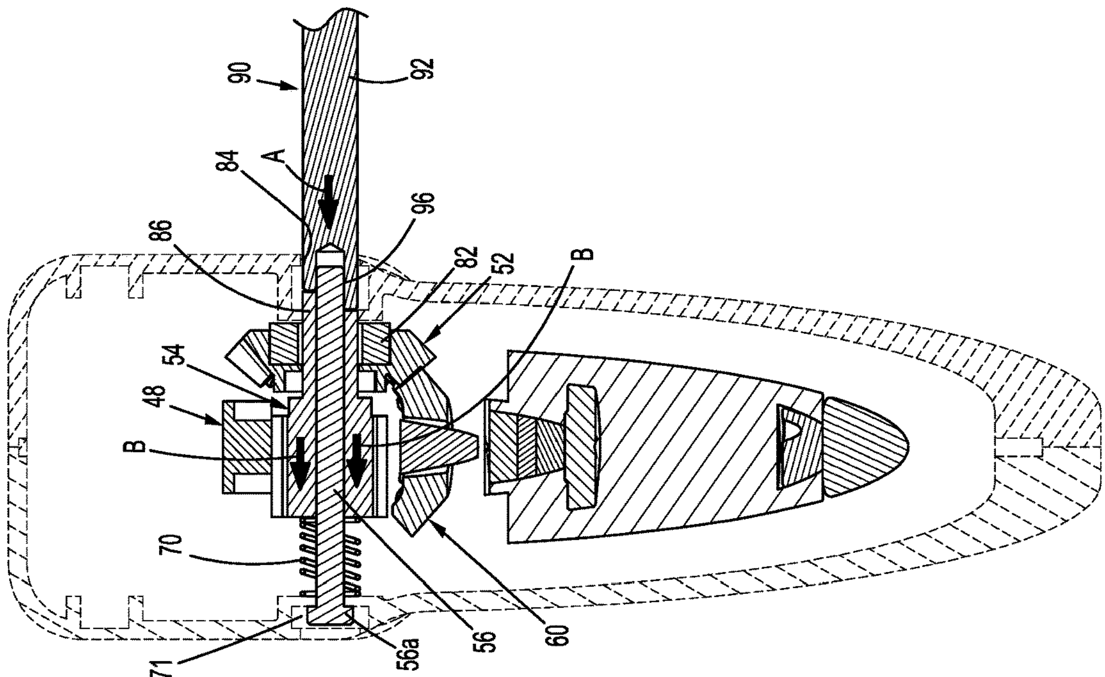
FIG. 9 is a cross-sectional view taken along section line 9-9 of FIG. 8.
Figure 8:
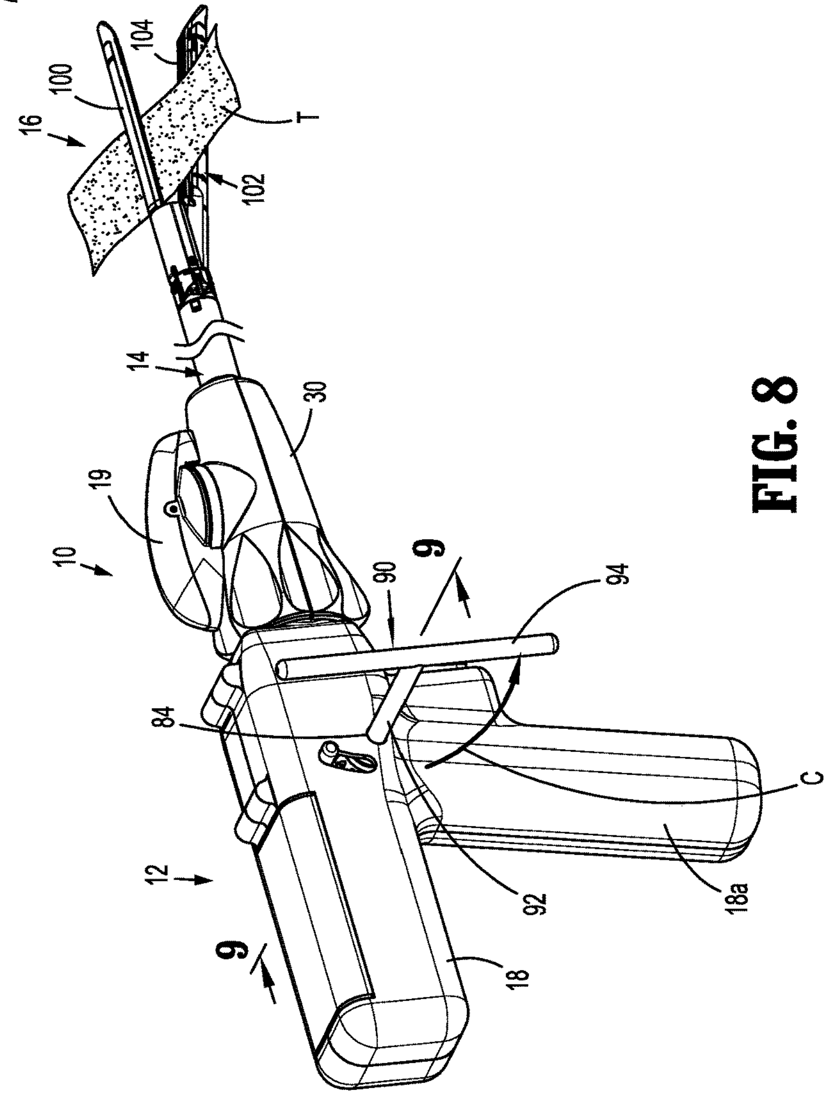
FIG. 8 is a side perspective view of the surgical device shown in FIG. 7 in an unclamped position with the retraction tool engaged with the handle assembly.

FIGS. 8 and 9 illustrate the stapling device 10 with the spur gear 54 moved to the second position. When the powered stapling device malfunctions and power is lost to the motor assembly 46 or the device becomes disabled, the retraction tool 90 can be used to retract the firing rod 50 (FIG. 2) to move the tool assembly 16 from the clamped position to the unclamped position. To manually retract the firing rod 50, the shaft 92 of the retraction tool 90 is inserted into the opening 84 in the housing 18 of the handle assembly 12 and into engagement with cylindrical shaft portion 72 of the spur gear 54. When the end of the shaft 92 of the retraction tool 90 engages the end of the cylindrical shaft portion 72 of the spur gear 54, the castellations 96 of the retraction tool 90 engage or mesh with the castellations 86 of the spur gear 54 to rotatably fix the retraction tool 90 to the spur gear 54. As the shaft 92 of the retraction tool 90 is inserted through the opening 84 in the direction of arrow "A" in FIG. 9, the spur gear 54 is moved from the first position to the second position in the direction of arrows "B" in FIG. 9. In the second position, the protrusions 76 (FIG. 4) of the spur gear 54 are moved from the cutouts 78 of the bevel gear 52 to disengage the spur gear 54 from the bevel gear 52. When the spur gear 54 disengages from the bevel gear 52, the retraction tool 90 can be rotated in the direction of arrow "C" in FIG. 8 to rotate the spur gear 54. The spur gear 54 remains engaged with the toothed rack 48 as the spur gear 54 moves from the first position to the second position such that rotation of the spur gear 54 causes retraction of the toothed rack 50 to retract the firing rod 50. When the firing rod 50 is retracted, the tool assembly 16 moves from the clamped position to the unclamped position.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A powered handle assembly for a surgical device comprising:
- a housing defining a cavity and an opening that communicates with the cavity;
- a motor assembly supported within the cavity of the housing and including a motor shaft and an output gear secured to the motor shaft;
- a toothed rack received within the cavity of the housing, the toothed rack supported for longitudinal movement between retracted and advanced positions;
- a gear shaft supported within the cavity of the housing;
- a spur gear rotatably supported on the gear shaft and linearly movable along the gear shaft between first and second positions, the spur gear including a gear member and a cylindrical shaft portion, the gear member engaged with the toothed rack such that rotation of the spur gear causes longitudinal movement of the toothed rack between the retracted and advanced positions; and
- a bevel gear rotatably supported about the gear shaft and engaged with the output gear of the motor assembly, the spur gear engaged with the bevel gear when the spur gear is in the first position and disengaged from the bevel gear when the spur gear is in the second position, wherein rotation of the bevel gear causes rotation of the spur gear when the spur gear is in the first position to move the toothed rack longitudinally between the retracted and advanced positions.

2. The powered handle assembly of claim 1, further including a biasing member positioned to urge the spur gear towards the first position.

3. The powered handle assembly of claim 2, further including a retraction tool dimensioned to be received through the opening in the housing to move the spur gear from the first position to the second position.

4. The powered handle assembly of claim 3, wherein the cylindrical shaft portion of the spur gear includes a first end spaced from the gear member that is configured to couple to the retraction tool such that rotation of the retraction tool with the spur gear in the second position causes rotation of the spur gear independently of the bevel gear.

5. The powered handle assembly of claim 4, wherein the retraction tool includes a shaft and a handle coupled to the shaft, the shaft of the retraction tool having a first end spaced from the handle that is configured to couple to the first end of the cylindrical shaft portion of the spur gear.

6. The powered handle assembly of claim 5, wherein the first end of the shaft of the retraction tool and the first end of the cylindrical shaft portion of the spur gear include castellations that engage each other such that rotation of the retraction tool causes corresponding rotation of the spur gear.

7. The powered handle assembly of claim 1, wherein the bevel gear is supported about the cylindrical shaft portion of the spur gear.

8. The powered handle assembly of claim 7, further including a bearing supported on the bevel gear and positioned about the cylindrical shaft portion of the spur gear.

9. The powered handle assembly of claim 1, wherein the spur gear supports protrusions, and the bevel gear defines cutouts, the protrusions received within the cutouts when the spur gear is in the first position to couple the spur gear to the bevel gear.

10. A surgical device comprising:
- a powered handle assembly including:
  - a housing defining a cavity and an opening that communicates with the cavity;
  - a motor assembly supported within the cavity of the housing and including a motor shaft and an output gear secured to the motor shaft;
  - a toothed rack received within the cavity of the housing, the toothed rack supported for longitudinal movement between retracted and advanced positions;
  - a gear shaft supported within the cavity of the housing;
  - a spur gear rotatably supported on the gear shaft and linearly movable along the gear shaft between first and second positions, the spur gear including a gear member and a cylindrical shaft portion, the gear member engaged with the toothed rack such that rotation of the spur gear causes longitudinal movement of the toothed rack between the retracted and advanced positions; and
  - a bevel gear rotatably supported about the gear shaft and engaged with the output gear of the motor assembly, the spur gear engaged with the bevel gear when the spur gear is in the first position and disengaged from the bevel gear when the spur gear is in the second position, wherein rotation of the bevel gear causes rotation of the spur gear when the spur gear is in the first position to move the toothed rack longitudinally between the retracted and advanced positions;
- an elongate body having a proximal portion and a distal portion, the proximal portion of the elongate body coupled to the powered handle assembly, the elongate body including a firing rod that is coupled to the toothed rack; and a tool assembly supported on the distal portion of the elongate body.

11. The surgical device of claim 10, wherein the tool assembly includes an anvil and a cartridge assembly.

12. The surgical device of claim 11, further including a biasing member positioned to urge the spur gear towards the first position.

13. The surgical device of claim 12, further including a retraction tool dimensioned to be received through the opening in the housing to move the spur gear from the first position to the second position.

14. The surgical device of claim 13, wherein the cylindrical shaft portion of the spur gear includes a first end spaced from the gear member that is configured to couple to the retraction tool such that rotation of the retraction tool with the spur gear in the second position causes rotation of the spur gear independently of the bevel gear.

15. The surgical device of claim 14, wherein the retraction tool includes a shaft and a handle coupled to the shaft, the shaft of the retraction tool having a first end spaced from the handle that is configured to couple to the first end of the cylindrical shaft portion of the spur gear.

16. The surgical device of claim 15, wherein the first end of the shaft of the retraction tool and the first end of the cylindrical shaft portion of the spur gear include castellations that engage each other such that rotation of the retraction tool causes corresponding rotation of the spur gear.

17. The surgical device of claim 11, wherein the bevel gear is supported about the cylindrical shaft portion of the spur gear.

18. The surgical device of claim 17, further including a bearing supported on the bevel gear and positioned about the cylindrical shaft portion of the spur gear.

19. The surgical device of claim 11, wherein the spur gear supports protrusions, and the bevel gear defines cutouts, the protrusions received within the cutouts when the spur gear is in the first position to couple the spur gear to the bevel gear.

20. The surgical device of claim 19, wherein the spur gear includes four protrusions, and the bevel gear defines four cutouts.

* * * * *